US006835851B2

(12) United States Patent
Monteil et al.

(10) Patent No.: US 6,835,851 B2
(45) Date of Patent: Dec. 28, 2004

(54) PROCESS FOR SYNTHESIZING N-(MERCAPTOACYL) AMINO ACID DERIVATIVES FROM ALPHA-SUBSTITUTED ACRYLIC ACIDS

(75) Inventors: Thierry Monteil, Saint Georges sur Fontaine (FR); Denis Danvy, Yvetot (FR); Jean-Christophe Plaquevent, Notre-Dame de Bondeville (FR); Pierre Duhamel, Mont-Saint-Aignan (FR); Lucette Duhamel, Mont-Saint-Aignan (FR); Jeanne-Marie Lecomte, Paris (FR); Jean-Charles Schwartz, Paris (FR); Serge Piettre, Saint-Martin l'Hortier (FR)

(73) Assignee: Bioprojet, Paris (FR)

( * ) Notice: Subject to any disclaimer, the term of this patent is extended or adjusted under 35 U.S.C. 154(b) by 119 days.

(21) Appl. No.: 09/986,629

(22) Filed: Nov. 9, 2001

(65) Prior Publication Data

US 2002/0055645 A1 May 9, 2002

(30) Foreign Application Priority Data

Nov. 9, 2000 (FR) .......................................... 00 14419

(51) Int. Cl.⁷ .............................................. C07C 61/00
(52) U.S. Cl. ........................ 562/400; 562/448; 564/162
(58) Field of Search ................................ 562/400, 448; 564/162

(56) References Cited

U.S. PATENT DOCUMENTS

| 4,401,667 A | * | 8/1983 | Wetzel et al. ............... 514/206 |
| 4,401,677 A | * | 8/1983 | Greenberg et al. ........... 514/562 |
| 4,474,799 A | * | 10/1984 | Greenberg et al. .......... 514/415 |
| 5,599,951 A | * | 2/1997 | Plaquevent et al. ......... 549/362 |
| 5,670,531 A | * | 9/1997 | Plaquevent et al. ......... 514/397 |
| 5,846,956 A | * | 12/1998 | Plaquevent et al. ......... 514/100 |

FOREIGN PATENT DOCUMENTS

| EP | 0 419 327 | 9/1990 |
| EP | 0 729 936 | 3/1996 |

* cited by examiner

*Primary Examiner*—Rita Desai
*Assistant Examiner*—Hector M. Reyes
(74) *Attorney, Agent, or Firm*—Stites & Harbison PLLC; B. Aaron Schulman

(57) ABSTRACT

The instant invention relates to a process for preparing a compound of formula (I):

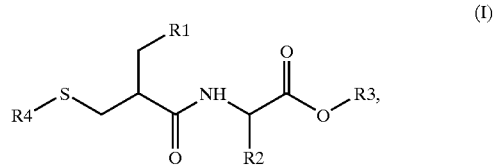

said process comprising a step (B) which consists in performing a Michael addition of a thioacid RS4H on to an α-substituted acrylamide derivative.

The invention also relates to the enantioselective synthesis of compounds of formula (I) wherein R2 is other than H, in the preferential (S, S) configuration:

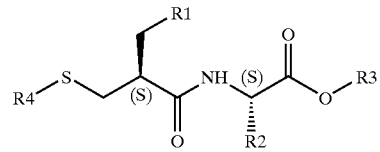

17 Claims, No Drawings

PROCESS FOR SYNTHESIZING N-(MERCAPTOACYL) AMINO ACID DERIVATIVES FROM ALPHA-SUBSTITUTED ACRYLIC ACIDS

The instant invention is connected with an industrial process for preparing N-(mercaptoacyl) amino acid derivatives from α-substituted acrylic acids.

The invention relates more particularly to a novel process for synthesizing N-(mercaptoacyl) amino acid derivatives of general formula (I):

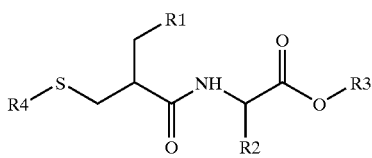

wherein

R1 represents:
- a phenyl group; or
- a 3,4-methylenedioxyphenyl group

R2 represents a hydrogen atom or a lower alkyl group;

R3 represents a hydrogen atom, a lower alkyl group or a lower phenylalkylene group; and R4 represents a linear or branched aliphatic acyl radical or an aromatic acyl radical.

In the scope of the present invention, the expression "lower alkyl group" means an alkyl group with linear or branched chain(s), which contains from 1 to 6 carbon atoms, and preferably from 1 to 4 carbon atoms.

Similarly, in the scope of the invention, the expression "lower alkylene group" means an alkylene group containing from 1 to 6 carbon atoms, and preferably from 1 to 4 carbon atoms.

The compounds of formula (I) have advantageous pharmacological properties. Thus, they especially exert inhibitory activity on some enzymes, such as neutral endopeptidase (EC 3.4.24.11) and angiotensin converting enzyme (EC 3.4.15.1). Administration of the compounds of formula (I) thus makes it possible to reduce or suppress the activity of these enzymes, which are responsible, respectively, for the inactivation of encephalins, of natriuretic atrial factor, and for the conversion of angiotensin I into angiotensin II. In therapy, these compounds exert antihypertensive or intestinal antisecretory activities and are used in the treatment of chronic cardiac insufficiency. Furthermore, such compounds may also be used in the treatment of osteoporosis, as it has especially been described in international patent application WO 94/21242.

As compounds of formula (I) which are particularly advantageous, mention may be made of the following two compounds:

1) racecadotril (benzyl N-(RS)-[2-acetylthiomethyl-1-oxo-3-phenylpropyl]glycinate), of formula (II):

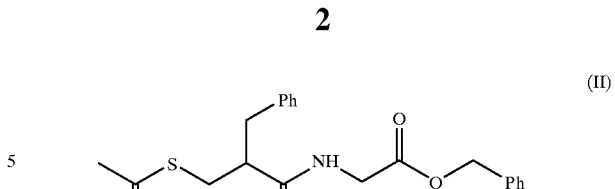

2) fasidotril (benzyl N-(S)-[2-acetylthiomethyl-1-oxo-3-(3,4-methylenedioxyphenyl)propyl]-(S)-alaninate), of formula (III):

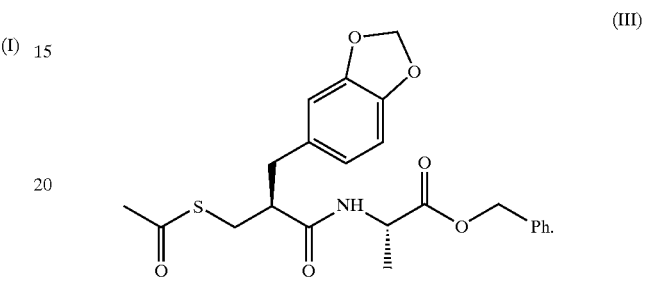

As regards compounds of formula (I) such as racecadotril of formula (II), their preparation and their therapeutic use, reference may be made to patent application EP 0 038 758.

Similarly, reference may be made to patent application EP 0 419 327 as regards the preparation and therapeutic applications of compounds of formula (I) such as fasidotril of formula (III).

More generally, a process for preparing the compounds of formula (I) from α-substituted acrylic acids is described in patent application EP 0 729 936. This process specifically involves a first step of Michael addition of a thioacid onto the α,β-unsaturated group C=C—C=O of the acrylic acid, followed by a second step of peptidic coupling of an amino ester onto the —COOH group in the presence of a coupling agent such as DCC (dicyclohexylcarbodiimide).

The synthetic process described in EP 0 729 936 is relatively efficient. Besides, it is advantageous with regard to its cost, especially due to the fact that it implements starting materials which are not expensive. However, because of the use of a coupling agent in its second step, this process generally induces the formation of side products such as dicyclohexylurea. These side products do not lead to major problems on a laboratory scale, wherein a purification by chromatography may be contemplated, but the side products are extremely hard to remove on an industrial scale.

Consequently, efforts have been made to modify the nature of the peptidic coupling step so as to avoid the formation of side products associated with the use of the coupling agent. In the regard, one contemplated alternative consists e.g. in converting the —COOH group into an acid chloride group, and in subsequently carrying out the coupling in the absence of coupling agent. However, even of this alternative does actually avoid the formation of side products such as dicyclohexylurea, it appears that the step for preparing the acid chloride often induces the formation of other side products thiol and disulphide, in appreciable amounts, which are also hard to separate out on an industrial scale.

Thus, it appears that, even if the preparation of N-(mercaptoacyl)amino acid derivatives from α-substituted acrylic acids by Michael addition of a thio acid and peptide coupling of an amino ester is relatively advantageous on a laboratory scale, such a reaction is generally difficult to adapt for an industrial use.

Now, the inventors have surprisingly discovered, that, by specifically implementing the peptidic coupling step before the Michael addition step, it is possible to render the process suitable for an industrial use, because the necessary purification steps are made earlier. As a matter of fact, the inventors' studies have shown that, contrary to the acid chloride intermediate obtained after the preliminary step of addition of the thioacid, which cannot be purified on industrial scale, the acid chloride directly obtained from the acrylic acid is distillable, which allows the improvement of the purity of the obtained N-(mercaptoacyl)amino acid derivatives, even in an industrial process.

Moreover, the inventors have discovered that, when the carbon to which the amino group —NH$_2$ is attached is specifically an asymmetric carbon in the amino ester used, the preliminary coupling with the amino ester furthermore induces an enantioselectivity for the subsequent Michael addition reaction. This property may be advantageously exploited in the context of the synthesis of compounds of formula (I) wherein R2 represents a lower alkyl group, such as, for example, fasidotril of formula (III). As a matter of fact, by using an amino ester containing an (S) asymmetric carbon, compounds of formula (I) are preferentially synthesized in their therapeutically advantageous (S, S) form during the Michael addition.

On the basis of this discoveries, the invention first aims at providing a process for preparing N-(mercaptoacyl)amino acid derivatives of formula (I) which may be exploited on an industrial scale, and which is advantageous not only with regard to its cost but also to the yield and purity of the obtained compounds.

Another aim of the invention is to provide a process for an enantioselective preparation of compounds of formula (I), wherein R2 is a lower alkyl group, preferentially leading to the formation of compounds of formula (I) in the (S, S) form below:

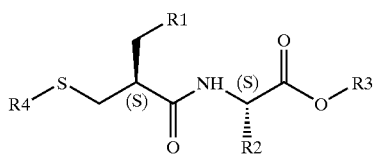

wherein R1, R2, R3 and R4 have the abovementioned meaning.

Thus, one subject of the present invention is a process for preparing a compound of formula (I):

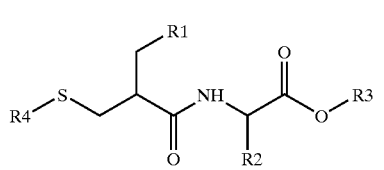

wherein R1, R2, R3 and R4 have the abovementioned meaning,
said process comprising a step (B), which consists in performing a Michael addition of a thioacid of formula (IV):

R4SH    (IV)

wherein R4 has the abovementioned definition, with an α-substituted acrylamide derivative of formula (V):

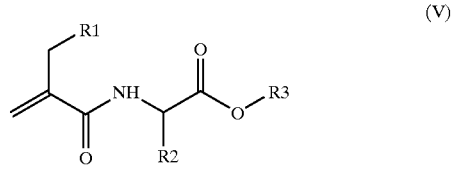

wherein R1, R2 and R3 have the same meaning as in formula (I).

Said Michael addition step (B) may be carried out in the presence or in the absence of a solvent. When a solvent is used, it is advantageously chosen from toluene, dichloromethane, 1,2-dichloroethane, water, chloroform, N,N-dimethylformamide, 1,4-dioxane, N-methylpyrrolidone, N,N-dimethylacetamide, butyl acetate, ethyl acetate, isobutyl acetate, isopropyl acetate, methyl acetate, propyl acetate, tetrahydrofuran, 1,4-dioxane, cyclohexane, isopropanol, n-propanol, acetone, 1-butanol and 2-butanol.

As a general rule, step (B) is moreover carried out at a temperature of between −20° C. and 130° C., advantageously between 15° C. and 115° C., and for a period generally of between 1 hour and 24 hours and preferably between 1 hour and 6 hours.

The compound of formula (I) which is prepared in step (B) may then be extracted from the reaction medium by any means known to the skilled person. Thus, in the context of using a solvent, said solvent may e.g. be, partially evaporated off, and the compound of formula (I) may then be obtained by crystallization in another solvent, for example in isopropyl alcohol and/or in isopropyl ether, and by filtration and washing.

Advantageously, the thioacid of formula (IV) used in the Michael addition of step (B) is thioacetic acid, thiobenzoic acid or thiopivalic acid. In other words, the group R4 preferably represents an acetyl radical CH$_3$—CO—, a benzoyl radical C$_6$H$_5$—CO— or a pivaloyl radical (CH$_3$)$_3$—CO—.

The α-substituted acrylamide of formula (V) used in step (B) is itself generally obtained from an α-substituted acrylic acid of formula (VI):

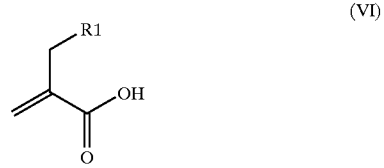

wherein R1 has the abovementioned definition.

As a matter of fact, these acrylic acids of formula (VI) are inexpensive compounds which are relatively simple to synthesize. For further details regarding an advantageous process for preparing these compounds, reference may be made especially to patent application EP 0 729 936.

In this case, the α-substituted acrylamide of formula (V) is generally obtained from a step (A) prior to step (B), comprising a step consisting in coupling the acrylic acid of formula (VI) with an amino ester of formula (VIII)

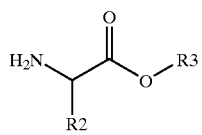

(VIII)

wherein R2 and R3 have the abovementioned definition.

In the general case, the acrylic acid (VI) may advantageously obtained from a preparation process as described in EP 0 038 758.

Step (A) of coupling of the acrylic acid and of the amino ester may be carried out by any means known to the skilled person. However, in order to lead to the formation of an α-substituted acrylamide (V) of high purity, step (A) advantageously comprises the successive steps consisting in:

(A1) reacting the said α-substituted acrylic acid of formula (VI) with a chloro acid, which is generally inorganic, so as to obtain an acid chloride of formula (VII):

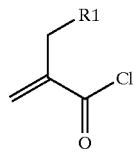

(VII)

in which R1 has the abovementioned definition; and (A2) reacting the acid chloride of formula (VII) so obtained with the amino ester of formula (VIII), in the presence of a base, so as to achieve the coupling.

Generally, the chloro acid used in step (A1) is then chosen from $SOCl_2$, $ClCO-COCl$, $PCl_3$ and $PCl_5$, and advantageously from $SOCl_2$ and $ClCO-COCl$, optionally in combination with dimethylformamide. This acid may be used alone or in the presence of an organic solvent preferably chosen, when one is used, from toluene, a xylene, a chlorobenzene, dichloromethane and mixtures of these solvents. Advantageously, when the chloro acid is used in the presence of a solvent, this solvent is toluene.

Moreover, irrespective of the nature of the inorganic chloro acid used, step (A1) is generally performed at a temperature of between 0° C. and 130° C. and preferably between 15° C. and 120° C. In the context of the use of toluene, the reaction is generally carried out under toluene reflux conditions. The acid chlorination reaction may be performed by gradual addition of the chloro acid, where appropriate over a period generally of between 5 minutes and 7 hours, or by direct addition of the chloro acid. However, in any case, an excess of inorganic acid is generally used, and preferably an amount of inorganic acid of between 1 and 2 molar equivalent(s) relative to the acrylic acid, and the reaction is generally allowed to continue for a period of between 30 minutes and 5 hours after the addition of the halo acid.

The acid chloride of formula (VII) obtained from step (A1) is advantageously subjected to a purification step before being used in step (A2). In this respect, it should be pointed out that, due to its chemical structure, the acid chloride (VII) obtained after step (A1) may be subjected to a distillation step before the coupling step (A2). It should be noted that such a distillation step is compatible with an industrial use. In fact, the acid chloride (VII) is generally distilled before step (A2), preferably under a reduced pressure generally of between 100 and 3 000 Pa (i.e. between 0.001 and 0.03 bar) and at a temperature advantageously of between 70° C. and 160° C. It should be pointed out that this possibility of distillation makes it possible at the end to obtain compounds of formula (I) of increased purity by removing the side products which may be present after the chlorination step.

Step (A2) of formation of the peptide bond is specifically performed in the presence of a base. Preferably, this base is an organic base, and more preferentially, it is an organic amine advantageously chosen from triethylamine and diisopropylethylamine.

Moreover, it should also be noted that, especially so as to improve the coupling yield, the amino ester used in step (A2) is itself generally introduced in the form of a salt, and preferably in the form of a salt of formula (VIIIa):

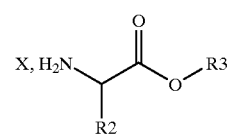

(VIIIa)

wherein R2 and R3 have the abovementioned definitions, and in which X is chosen from HCl , $CH_3SO_3H$ and 4-methylphenyl-$SO_3H$.

Step (A2) is generally carried out in the presence of an organic solvent generally chosen, when one is used, from toluene, dichloromethane, 1,2-dichloroethane, chloroform, N,N-dimethylformamide, 1,4-dioxane, N-methylpyrrolidone, N,N-dimethylacetamide, butyl acetate, ethyl acetate, isobutyl acetyl, isopropyl acetate, methyl acetate, propyl acetate and tetrahydrofuran.

It should be pointed out that the addition reaction of the acid chloride (VII) to the amino ester (VIII) or its salt (VIIIa) performed in step (A2) is generally highly exothermic. Consequently, step (A2) is generally carried out at a low temperature, advantageously between −10° C. and 25° C., and the reaction is preferably carried out by gradual addition of the acid chloride (VII) in a medium maintained at the desired reaction temperature and containing the amino ester or the amino ester salt, and the base. As a general rule, the base is used in an amount of greater than two molar equivalents relative to the amount of acid chloride introduced. The amino ester (VIII) itself is advantageously used in slight excess relative to the acid chloride (VII), and preferably in an amount of between 1 and 1.2 molar equivalents relative to the acid chloride. Preferably, the acid chloride is added over a period of between 30 minutes and 3 hours, and the addition reaction is generally allowed to continue at the chosen working temperature for a period advantageously of between 15 minutes and 3 hours.

Once the addition is complete, the product (VI) resulting from the reaction is generally isolated by extraction, where appropriate by washing the reaction medium with water and/or with an acidic aqueous solution, followed by separation of the organic phase. Advantageously, the organic phase is then subjected to one or more subsequent washes with water and/or with aqueous solutions, that are preferably acidic. The solvent present is then generally removed, for example by evaporation and/or by crystallization of compound (VI), filtration and drying.

According to one particularly advantageous embodiment of the process of the invention, compound (V) used in step (B) is a chiral compound wherein R2 specifically denotes a lower alkyl group obtained, for example, by coupling a chiral amino ester of formula (VIII) containing the same group R2 and an acrylic acid of formula (VI).

In this case, since R2 is not a hydrogen atom, the carbon atom to which the group R2 is attached is specifically an asymmetric carbon. Consequently, compound (V) is a chiral compound. The orientation of the group R2 in this compound thus induces a stereo-selectivity for the Michael reaction of the subsequent step (B). Consequently, compound (V) is preferably used at least predominantly in its S configuration or at least predominantly in its R configuration.

In a particularly advantageous manner, in compound (V), the asymmetric carbon linked to the group R2 is a carbon in the S configuration. As a matter of fact, in this case, the compound of formula (I) predominantly obtained after step (B) is a compound (I) in the (S, S) configuration which has advantageous therapeutic activity, especially inhibitory activity on certain enzymes, such as neutral endopeptidase and angiotensin conversion enzyme. Thus, in the context of preparing fasidotril of formula (III), the use of benzyl (S)-alaninate as amino ester of formula (VIII) leads to the preferential formation of the corresponding compound (I), predominantly in the (S, S) form of formula (III), whereas the (R, S) form, which is of no therapeutic value, is obtained in minor amounts.

The use of a compound (V) in the (R) configuration leads, in the same way, to the predominant production of a compound (I) of (R, R) configuration. However, such (R, R) compounds generally do not have any advantageous therapeutic activity.

Consequently, compound (V) is preferably used in its optically pure S form so as to promote the formation of compounds (I) of (S, S) configuration. In that case, compound (V) is generally prepared by a condensation reaction of an acrylic acid of formula (VI) with an amino ester of formula (VIII) derived from a natural amino acid such as alanine, which naturally possesses a lower alkyl group on a carbon in the S configuration.

So as to quantify the stereoselectivity of the Michael reaction of step (B), it should be noted that it is generally possible to define, for the compounds of formula (I) obtained after step (B), an enantiomeric excess S:R expressed by the molar ratio:

$$(n_S - n_R)/(n_S + n_R),$$

wherein:

$n_S$ represents the number of moles of compound (I) in which the carbon bearing the group —CH$_2$—R1 is in the S configuration;

and $n_R$ represents the number of moles of compound (I) in which the carbon bearing the group —CH$_2$—R1 is in the R configuration.

As a general rule, when R2 is a hydrogen atom, this S:R enantiomeric excess is zero, and the two enantiomers R and S have an equal chance of being formed during the Michael addition in step B. Thus, for example, racecadotril of formula (II) obtained from a compound (V) in which R2=H, is synthesized in the form of a racemic mixture by the process of the invention.

On the other hand, when R2 is not a hydrogen atom, the chirality of compound (V) induces an enantioselectivity for the Michael reaction. Consequently, during the specific use of a reaction intermediate of chiral (V) type at least predominantly in its S configuration or at least predominantly in its R configuration, the S:S enantiomeric excess observed for the compounds (I) obtained in step (B) is non-zero.

Thus, in the context of the use of an optically pure acrylamide derivative wherein the asymmetric carbon linked to the group R2 is a carbon of S configuration, obtained, for example, by coupling an amino ester (VIII) of (S) configuration with an acrylic acid (VI), the S:R enantiomeric excess defined above (which is then an (S, S):(R, S) diastereomeric excess) is generally greater than 10%, and may in certain cases even be greater than 25%, or even greater than 30%.

Nevertheless, in the context of the use of chiral compounds (V), so as to further improve the reaction stereoselectivity, it is possible, in some cases, to implement chirality inducers in the Michael reaction of step (B). Such chirality inducers may be, for example, quinquina alkaloids such as, for example, quinine, quinidine, cinchonine or cinchonidine, or derivatives of these compounds such as, for example, o-acetylquinine, and, where appropriate, preferably in a proportion of from 0.01 to 1 equivalent relative to compound (V). In the general case, the presence of such compounds is, however, absolutely not necessary to obtain an enantiomeric excess of greater than 15%.

Moreover, when R2 is specifically a lower alkyl group which conters a chiral nature to the carbon to which it is attached, the process of the invention may also comprise, after step (B), a subsequent step (C) of separation of the diastereoisomers obtained in step (B).

Thus, in the context of the use of a compound (V) in the (S) configuration preferentially used, a step of separation of the diastereoisomers in the (S, S) and (R, S) configurations obtained after step (B) can generally be performed by selective crystallization of the (S, S) compound, where appropriate in a solvent or a mixture of solvents advantageously chosen from isopropanol, n-propanol, ethanol, methanol, diisopropyl ether, toluene, dichloromethane, chloroform, 1,4-dioxane, butyl acetate, ethyl acetate, isobutyl acetate, isopropyl acetate, methyl acetate, propyl acetate, tetrahydrofuran, 1,4-dioxane, cyclohexane, acetone, 1-butanol, 2-butanol, cyclohexane and 1,2-dimethoxyethane.

The characteristics and advantages of the process of the invention will emerge even more clearly in the light of the illustrative examples given below.

EXAMPLE 1

Preparation of racecadotril of formula (II) (benzyl N-(RS)-[2-acetylthiomethyl-1-oxo-3-phenyl-propyl] glycinate)

Step (A): Preparation of benzyl N-[1-oxo-2-benzyl-propenyl]glycinate.

Step (A1): Synthesis of 2-benzylpropenoyl Chloride

The following were introduced into a 500 ml conical flask:

71.49 g (i.e. 441.29 mmol) of benzylacrylic acid; and 179 ml of toluene.

The obtained mixture was heated to a temperature of 110° C. and about 35 ml of toluene were distilled off, so as to dry the benzylacrylic acid by azeotropic extraction.

The temperature was then allowed to stabilize at 70° C., followed by addition over a period of 5 hours of 64.06 g (i.e. 538.32 mmol) of thionyl chloride SOCl$_2$. The temperature was maintained at 70° C. throughout the addition period.

After the addition, the reaction mixture was maintained for 3 hours at 70° C.

The temperature was then allowed to decrease to room temperature (25° C.) and the reaction medium was then concentrated by evaporating off the toluene on a rotary evaporator under vacuum.

82.8 g of an orange-yellow oil were thus obtained.

The oil was then distilled under vacuum, by using a water pump (15 mmHg), while heating with an oil bath at a temperature of between 145 and 150° C.

72.71 g of a colourless oil were thus obtained.

Boiling point: 115° C.

Yield for step (A1): 91%.

Step (A2): Coupling with Benzyl Para-toluenesulphonate Glycinate

The following were introduced into a 250 ml conical flask:

45.18 g (i.e. 134.06 mmol) of benzyl para-toluenesulphonate glycinate; and 110 ml of toluene.

The suspension was stirred and cooled by immersion in a bath of ice at 0° C.

27.08 g (i.e. 268.11 millimol) of triethylamine were added over 30 minutes, while maintaining the temperature at 0° C.

Once the medium became clear, the temperature was maintained at 0° C. for 30 minutes.

22 g (i.e. 121.88 millimol) of the acid chloride obtained in the form of a colourless oil in the above step (A1) were then added, with stirring and progressively (over one hour), while maintaining the conical flask in a bath of ice at 0° C. throughout, due to the exothermicity of the reaction.

The reaction mixture was stirred for one hour at 0° C. and the temperature was then allowed to rise to 25° C.

45 ml of distilled water were then added to the medium, followed by acidification at a pH of 4 by adding 5N hydrochloric acid. The mixture was stirred for 5 minutes and the two phases obtained were then poured into a separating funnel. The organic phase was separated out and then washed successively with:

1) 90 ml of water
2) 45 ml of aqueous sodium bicarbonate solution at 44 g per liter
3) 45 ml of water.

The organic phase was then concentrated on a rotary evaporator under vacuum so as to remove the solvent.

The concentrated mixture obtained was dissolved in 110 ml of a mixture of 75/25 by volume isopropyl ether and isopropyl alcohol. The solution obtained was stirred and then cooled. A crystallization began at 8° C. and was then found to be very rapid. The mixture was left stirring for 30 minutes at 5° C.

The product was filtered off, spin-dried and rinsed with 20 ml of isopropyl ether at 5° C., so as to obtain 30.51 g of a wet solid which was dried under vacuum (20 mmHg) until a constant mass was obtained.

30.0 g of a white solid were obtained.

Melting point=52–53° C.

TLC: 50/50 ethyl ether/petroleum ether eluent, one single spot; Rf=0.5.

Yield for step (A2)=79%.

Step (B): Michael Addition of Thioacetic Acid.

30 g (i.e. 97.08 mmol) of the white solid obtained after step (A2) were introduced into a 250 ml conical flask equipped with a magnetic stirrer.

8.85 g (116.44 mmol) of thioacetic acid were then gradually added with stirring, at 25° C., over a period of 30 minutes.

The temperature of the reaction medium was then raised to 80° C. and this temperature was maintained for 3 hours.

The temperature was then reduced to 40° C. and 19 ml of isopropyl alcohol were added. The mixture was then evaporated under vacuum on a rotary evaporator. The oily residue obtained was dissolved in 150 ml of isopropyl alcohol and brought to 40° C. The mixture was stirred and allowed to cool slowly. The first crystals were observed to appear at a temperature of 27° C. The temperature was then maintained at 27° C. for 45 minutes, followed by cooling to 10° C.

The crystalline solid obtained was filtered off on a sinter funnel of porosity No. 2, spin-filtered and then rinsed with 50 ml of a mixture of isopropyl ether and isopropyl alcohol (3/2 by volume) at 5° C.

A white solid was thus obtained, which was dried at 45° C. under vacuum (15 mmHg).

Mass obtained: 28.22 g.

Melting point=79–80° C. (microscope)

TLC: 50/50 ethyl ether/petroleum ether eluent, one single spot; Rf=0.45.

Yield for step (B)=75%.

Overall yield for the process for preparation of racecadotril: 53.9%.

EXAMPLE 2

Preparation of fasidotril of formula (III) (benzyl N-(S)-[2-acetylthiomethyl-1-oxo-3-(3,4-methyl-enedioxyphenyl)propyl]-(S)-alaninate Step (A): Preparation of benzyl N-[1-oxo-2-(3,4-methyl-enedioxybenzyl)propenyl]-(S)-alaninate.

Step (A1): Synthesis of 2-(3,4-methylenedioxy-benzyl) propenoyl chloride:

The following were introduced into a 250 ml three-necked flask:

50 g (i.e. 242.71 millimol) of piperonylacrylic acid; and 50 ml of toluene.

34.66 g (i.e. 291.26 millimol) of thionyl chloride were added over a period of 5 minutes.

The suspension prepared was refluxed using an oil bath for 30 minutes.

The reaction medium was then allowed to cool to room temperature (25° C.) and was then concentrated on a rotary evaporator in a water bath at 45° C.

A crude orange-red coloured oil was thus obtained.

Mass=56.95 g.

Step (A2): Coupling with Benzyl Methanesulphonate Alaninate

The following were introduced into a one liter three-necked flask:

150 ml of toluene; and 66.75 g (i.e. 242.72 mmol) of benzyl methane-sulphonate alaninate.

The suspension obtained was stirred and cooled to 5° C.

51.48 g (509.70 mmol) of triethylamine were then added over 15 minutes.

The mixture was stirred for 10 minutes at a temperature of between 0 and +5° C.

56.95 g of crude oil obtained from step (A1) dissolved in 50 ml of toluene were then added slowly to the medium, without exceeding 15° C in the bulk during the addition. Given the very high exothermicity of the reaction, the addition was carried out over 40 minutes while maintaining the three-necked flask in a bath of ice containing salt, at −5° C.

The reaction medium was then allowed to warm to room temperature (25° C.) over about 20 minutes. 150 ml of water were then added and the mixture was stirred for 5 minutes.

The two phases obtained were transferred into a separating funnel and the aqueous phase was removed.

The toluene phase was then washed successively with:

100 ml of 1N HCl 150 ml of water.

The organic phase was then concentrated on a rotary evaporator in a water bath at 50° C.

87.16 g of an oily residue were obtained, and were dissolved in 27 ml of isopropanol.

100 ml of isopropyl ether were then added.

The solution obtained was transferred into a beaker and then cooled to 10° C. and stirred.

The medium was then seeded with 5 mg of benzyl N-[1-oxo-2-(3,4-methylenedioxybenzyl)propenyl]-(S)-alaninate in crystalline form.

The medium was then cooled to 5° C. and stirred for 30 minutes.

The crystalline solid formed was filtered off on a sinter funnel of porosity No. 2.

The precipitate was then re-slurried in 100 ml of isopropyl ether at 5° C. and then filtered off, after which it was rinsed with 25 ml of isopropyl ether at 5° C. and dried under vacuum to constant mass.

63.93 g of a cream-white solid are obtained.

Melting point: 51–52° C. (by microscope).

TLC: 50/50 ethyl ether/petroleum ether eluent; developer: phosphomolybdic acid; Rf=0.38.

Optical rotation: $[\alpha]_D=-16.7°$ (25° C., c=2.04 in methanol).

Yield for step (A): 71%.

Step (B): Michael Addition of Thioacetic Acid.

30 g (81.74 mmol) of the solid obtained from the preceding step were introduced into a 250 ml three-necked flask equipped with a magnetic stirrer.

7.76 g (i.e. 102.10 mmol) of thioacetic acid were then gradually introduced, at 25° C. and over a period of 5 minutes, with stirring.

The reaction medium was then heated at 80° C. for 2 to 3 hours.

The oily medium thus obtained was subjected to an analysis by $^1$H NMR and HPLC, so as to monitor the end of the reaction. The (S, S):(R, S) diastereoisomeric excess in the reaction medium was thus measured and was equal to 25%.

Step (C1): First recrystallization.

300 ml of isopropanol were then added to the reaction medium obtained from step (B), and the solution obtained was cooled to 30° C.

The medium was then seeded with 50 mg of crystalline (S, S) fasidotril and the temperature was maintained at 30° C. for 2 hours.

The solid obtained was filtered off and rinsed with 15 ml of isopropanol, and then dried under vacuum (20 mmHg) at 25° C.

13.88 g of a white solid were thus obtained.

Melting point: 97–100° C.

TLC: eluent: 60/40 ethyl ether/petroleum ether; Rf=0.44, one single spot; developer: UV 254 nm and phosphomolybdic acid.

$^1$H NMR: the $^1$H NMR reveals an (S, S):(S, R) diastereoisomeric excess of about 90%.

Overall yield for steps (B) and (C1): 38%.

Step (C2): Second recrystallization.

The 13.88 g of white solid obtained previously and 207 ml of isopropanol were introduced into a 250 ml three-necked round-bottomed flask.

The mixture was stirred and heated at a temperature of 70° C. until the solid was completely dissolved.

The solution obtained was then cooled to 50° C. and selective crystallization of the (S, S) compound was initiated by introduction of a few crystals of (S, S) fasidotril.

The medium was then cooled to 35° C. over 2 hours and the temperature was then maintained at 35° C. for 1 hour 30 minutes.

The crystalline solid obtained was then filtered off on a sinter funnel of porosity No. 2 and rinsed with 15 ml of isopropanol.

After drying under vacuum (20 mmHg) at 25° C., 11.16 g of a solid were thus obtained.

Melting point: 109° C. (microscope) (S, S):(R,S) diastereomerisomeric excess: at least equal to 98%.

TLC: eluent: 60/40 ethyl ether/petroleum ether; developer:

UV 254 nm and phosphomolybdic acid; Rf=0.42.

Optical rotation: $[\alpha]_D=-51.8°$ (20° C., c=1.03 in methanol).

Yield for step (C): 80%.

Overall yield for the process for preparation of fasidotril: 30%.

What is claimed is:

1. A process for preparing a compound of formula (I):

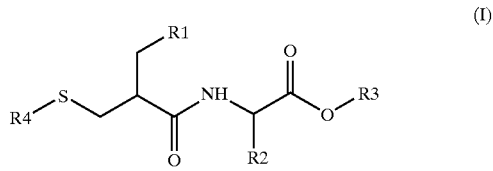

wherein:

R1 represents:
  a phenyl group; or
  a 3,4-methylenedioxyphenyl group;

R2 represents a hydrogen atom or a lower alkyl group;

R3 represents a lower alkyl group or a lower phenylalkylene group; and

R4 represents a linear or branched aliphatic acyl radical or an aromatic acyl radical, said process comprising step (B) performing a Michaël addition of a thioacid of formula (IV):

wherein R4 has the same meaning as in formula (I), with an α-substituted acrylamide derivative of formula (V):

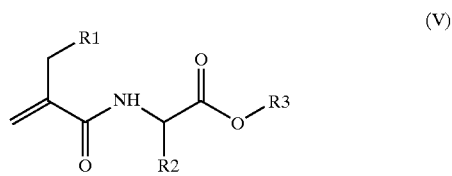

wherein R1, R2 and R3 have the same meaning as in formula (I).

2. The process according to claim 1, wherein the group R4 represents an acetyl radical $CH_3$—CO—, a benzoyl radical $C_6H_5$—CO— or a pivaloyl radical $(CH_3)_3$—CO—.

3. The process according to claim 1 which further comprises the step (A), prior to step (B), wherein step (A) comprises coupling an acrylic acid of formula (VI):

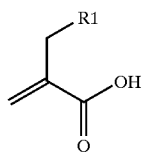

wherein R1 has the same meaning as in formula (I), with an amino ester of formula (VIII):

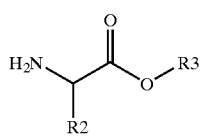

wherein R2 and R3 have the have the same meaning as in formula (I).

4. The process according to claim 3, wherein the coupling of the acrylic acid (VI) and of the amino ester (VIII) that is performed in step (A) comprises the successive steps:
(A1) reacting said α-substituted acrylic acid of formula (VI) with an chloro acid so as to obtain an acid chloride of formula (VII):

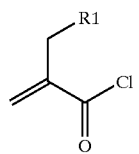

wherein R1 has the same meaning as in formula (I); and
(A2) reacting the acid chloride of formula (VII) thus obtained with said amino ester of formula (VIII), in the presence of a base, so as to achieve the coupling.

5. The process according to claim 4, wherein the chloro acid used in step (A1) is selected from the group consisting of $SOCl_2$, $ClCO-COCl$, $PCl_3$ and $PCl_5$.

6. The process according to claim 4, wherein the acid chloride of formula (VII) obtained from step (A1) is subjected to a distillation step before being used in step (A2).

7. The process according to claim 4, wherein the base used in step (A2) is an organic amine.

8. The process according to claim 4, wherein the amino ester used in step (A2) is introduced in the form of a salt of formula (VIIIa):

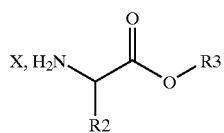

wherein R2 and R3 have the have the same meaning as in formula (I); and
wherein X is chosen from HCl, $CH_3SO_3H$ and 4-methylphenyl-$SO_3H$.

9. The process according to claim 4, wherein step (A2) is carried out in the presence of an organic solvent selected from the group consisting of toluene, dichloromethane, 1,2-dichloroethane, chloroform, N,N-dimethylformamide, 1,4-dioxane, N-methylpyrrolidone, N,N-dimethylacetamide, butyl acetate, ethyl acetate, isobutyl acetate, isopropyl acetate, methyl acetate, propyl acetate and tetrahydrofuran.

10. The process according to claim 1, wherein compound (V) used in step (B) is a chiral compound wherein R2 denotes a lower alkyl group, said compound (V) being used at least predominantly in its S configuration or at least predominantly in its R configuration.

11. The process according to claim 10, wherein compound (V) is used in its optically pure S form.

12. The process according to claim 11 which further comprises the step of preparing compound (V) by a condensation reaction of an acrylic acid of formula (VI) with an amino ester of formula (VIII) derived from a natural amino acid.

13. The process according to claim 10, wherein quinquina alkaloid or derivatives thereof are used in step (B).

14. The process according to claim 10, further comprising, after step (B), a subsequent step (C) of separating the diastereoisomers obtained in step (B).

15. The process according to claim 1, wherein said obtained compound of formula (I) is benzyl N-(RS)-[2-acetylthiomethyl-1-oxo-3-phenylpropyl]glycinate of formula (II):

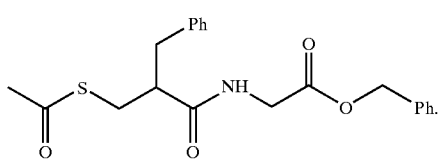

16. The process according to claim 1, wherein said obtained compound of formula (I) is benzyl N-(S)-[2-acetylthiomethyl-1-oxo-3-(3,4-methylenedioxyphenyl) propyl]-(S)-alaninate of formula (III):

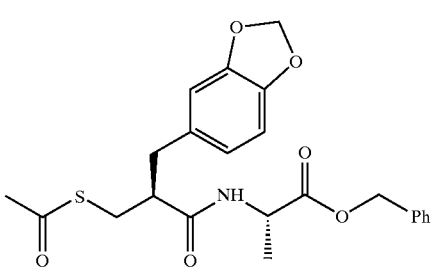

17. A process for preparing a compound of formula (I):

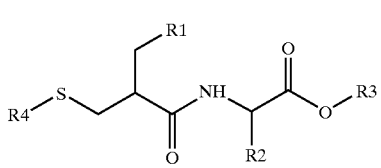

wherein:
R1 represents:
a phenyl group; or
a 3,4-methylenedioxyphenyl group;
R2 represents a hydrogen atom or a lower alkyl group;
R3 represents a lower alkyl group or a lower phenylalkylene group; and R4 represents a linear or branched aliphatic acyl radical or an aromatic acyl radical, said process comprising step (B) performing a Michaël addition a thioacid of formula (IV):

R4SH (IV)

wherein R4 has the same meaning as in formula (I), with an α-substituted acrylamide derivative of formula (V):

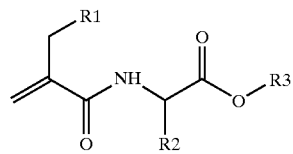

wherein R1 and R2 have the same meaning as in formula (I), R3 denotes a lower alkyl groups, said compound (V) being used at least predominantly in its S configuration or at least predominantly in its R configuration, and wherein quinquina alkaloid or derivatives thereof are used in step (B).

* * * * *